(12) United States Patent
Barrett et al.

(10) Patent No.: US 8,512,713 B2
(45) Date of Patent: Aug. 20, 2013

(54) MYXOMA VIRUS MUTANTS FOR CANCER TREATMENT

(75) Inventors: John W. Barrett, London (CA); Grant McFadden, Gainesville, FL (US)

(73) Assignee: Robarts Research Institute, London, Ontario (CA)

( * ) Notice: Subject to any disclaimer, the term of this patent is extended or adjusted under 35 U.S.C. 154(b) by 567 days.

(21) Appl. No.: 12/301,961

(22) PCT Filed: Jun. 1, 2007

(86) PCT No.: PCT/US2007/070219
§ 371 (c)(1),
(2), (4) Date: Sep. 7, 2010

(87) PCT Pub. No.: WO2007/143548
PCT Pub. Date: Dec. 13, 2007

(65) Prior Publication Data
US 2011/0158945 A1  Jun. 30, 2011

Related U.S. Application Data

(60) Provisional application No. 60/803,640, filed on Jun. 1, 2006.

(51) Int. Cl.
*A61K 39/275* (2006.01)
*C12N 7/01* (2006.01)

(52) U.S. Cl.
USPC ........................... 424/232.1; 435/235.1; 435/5

(58) Field of Classification Search
None
See application file for complete search history.

(56) References Cited

U.S. PATENT DOCUMENTS

| 7,582,614 B2 | 9/2009 | McFadden et al. |
| 2002/0098201 A1 | 7/2002 | McFadden et al. |
| 2006/0263333 A1 | 11/2006 | McFadden et al. |
| 2009/0035276 A1 | 2/2009 | McFadden et al. |

FOREIGN PATENT DOCUMENTS

| EP | 0 972 840 A2 | 1/2000 |
| WO | 99/18799 A1 | 4/1999 |
| WO | 2000/62735 A2 | 10/2000 |
| WO | 01/04318 A2 | 1/2001 |
| WO | 01/87324 A1 | 11/2001 |
| WO | 2004/078206 A1 | 9/2004 |
| WO | 2005/113018 A1 | 12/2005 |
| WO | 2007/143545 A2 | 12/2007 |
| WO | 2007/143548 A2 | 12/2007 |
| WO | 2007/147118 A1 | 12/2007 |

OTHER PUBLICATIONS

Lun, et al., "Myxoma Virus is a Novel Oncolytic Virus with Significant Antitumor Activity against Experimental Human Gliomas", Cancer Research, 65(21): 9982-9990, Nov. 2005.
Sypula, et al., "Myxoma virus tropism in human tumor cells", Gene Therapy and Molecular Biology, 8:103-114, 2004.
Barrett, et al., "Immunomodulatory Proteins of Myxoma Virus", Seminars in Immunology,13: 73-84, 2001.
Kim, et al., "Replication-selective Virotherapy for Cancer: Biological Principles, Risk Management and Future Directions", Nature Medicine, 7(7): 781-787, 2001.
Thorne, et al., "Vaccinia Virus and Oncolytic Virotherapy of Cancer", Current Opinion in Molecular Therapeutics, 7(4): 359-365, Aug. 2005.
Thorne, et al., "The Use of Oncolytic Vaccinia Viruses in the Treatment of Cancer: A New Role for an Old Ally?", Current Gene Therapy, 5: 429-443, Aug. 2005.
McFadden, "Poxvirus Tropism", Natural Reviews Microbiology, 3: 201-213, Mar. 2005.
Shen, et al., "Fighting Cancer with Vaccinia Virus: Teaching New Tricks to an Old Dog", Molecular Therapy, 11 (2):180-195, Feb. 2005.
Barcena, et al., "Isolation of an attenuated myxoma virus field strain that can confer protection against myxomatosis on contacts of vaccinates", Arch. Virol., 146: 759-771, 2000.
Cameron, et al., "The Complete DNA Sequence of Myxoma Virus", Virology, 264: 298-318, 1999.
Balachandran, et al., "Defective Translational Control Facilitates Vesicular Stomatitis Virus Oncolysis", Cancer Cell, 5: 51-65, Jan. 2004.
Stojdl, et al., "VSV Strains with Defects in their Ability to Shutdown Innate Immunity are potent Systemic Anti-Cancer Agents", Cancer Cell, 4: 263-275, Oct. 2003.
Kerr, et al., "Review: Immune Responses to Myxoma Virus", Viral Immunology,15(2), pp. 229-246, 2002.
Lalani, et al., "Role of the Myxoma Virus Soluble CC-Chemokine Inhibitor Glycoprotein, M-T1, during Myxoma Virus Pathogenesis", Virology, 256: 233-245, 1999.
Mossman, et al., "Myxoma Virus M-T7, a Secreted Homolog of the Interferon-gamma Receptor, Is a Critical Virulence Factor for the Development of Myxomatosis in European Rabbits", Virology, 215: 17-30, 1996.
Vile, et al., "The Oncolytic Virotherapy Treatment Platform for Cancer: Unique Biological and Biosafety Points to Consider", Cancer Gene Therapy, 9: 1062-1067, 2002.
Robinson, et al., "Progress towards using Recombinant Myxoma Virus as a Vector for Fertility Control in Rabbits", Reprod. Fertil. Dev., 9:77-83, 1997.
Bell, "Replicating Oncolytic Virus Therapeutics—Third International Meeting", IDrugs, 8(5): 360-363, May 2005.
Stanford, et al, "Oncolytic Virotherapy Synergism with Signaling Inhibitors: Rapamycin Increases Myxoma Virus Tropism for Human Tumor Cells", Journal of Virology, 81(3) 1251-1260, Feb. 2007.
Lun, et al., "Targeting Human Medulloblastoma: Oncolytic Virotherapy with Myxoma Virus is Enhanced by Rapamycin", Cancer Research, 67(18): 8818-8827, Sep. 2007.
Mossman, et al., "Disruption of M-T5, a novel Myxoma Virus Gene Member of the Poxvirus Host Range Superfamily, Results in Dramatic Attenuation of Myxomatosis in Infected European Rabbits", Journal of Virology, 70(7), 4394-4410, 1996.

(Continued)

*Primary Examiner* — Stacy B. Chen
(74) *Attorney, Agent, or Firm* — Lewis J. Kreisler

(57) ABSTRACT

Myxoma viruses that are deficient in the activity of a Myxoma virus protein selected from the group consisting of M11L, M063, M136, M-T4 and M-T7 are useful for treating cancer.

5 Claims, 5 Drawing Sheets

(56) References Cited

OTHER PUBLICATIONS

Mossman, et al., "The Myxoma Virus-soluble Interferon-gamma Receptor Homolog, M-T7, Inhibits Interferon-gamma in a Species-Specific Manner", Journal of Biological Chemistry, 270(7): 3031-3038, 1995.

Adams, et al., "Construction and Testing of Novel Host-range Defective Myxoma Virus Vaccine with the M063 Gene Inactivated that is Non-Permissive for Replication in Rabbit Cells", Veterinary Research, 39(60): 1-13, 2008.

Opgenorth, et al., "Deletion Analysis of Two Tandemly Arranged Virulence Genes in Myxoma Virus, M11L and Myxoma Growth Factor", Journal of Virology, 66(8): 4720-4731, Aug. 1992.

Lalani, et al., "The Purified Myxoma Virus Gamma Interferon Receptor Homolog M-T7 Interacts with the Heparin-Binding Domains of Chemokines", Journal of Virology, 71(6): 4356-4363, Jun. 1997.

Wang, et al., "Infection of human cancer cells with myxoma virus requires Akt activation via interaction with a viral ankyrin-repeat host range factor", PNAS, 103(12); 4640-4645, Mar. 2006.

Su, et al., "Myxoma Virus M11L Blocks Apoptosis through Inhibition of Conformational Activation of Bax at the Mitochondria", Journal of Virology, 80(3): 1140-1151, Feb. 2006.

Barrett, et al., "Myxoma Virus M063R is a Host Range Gene Essential for Virus Replication in Rabbit Cells", Virology, 36:123-132, 2007.

Barrett, et al., "Indentification of Host Range Mutants of Myxoma Virus with Altered Oncolytic Potential in Human Glioma Cells", Journal of Neuro Virology, 13: 549-560, 2007.

Barrett et al Abstract, "What is the role of Myxoma virus M135R?", Fourteenth International Poxvirus and Iridovirus Conference, Lake Placid, NY, 2002.

Barrett, "Characterization of myxoma virus host range in human glioma cells" FASEB Summer Research Conference, Indian Wells, California, Jun. 7, 2006 (Poster).

Barrett, et al., "Myxoma virus recombinants with improved potential as oncolytic agents", Poster presented at Oncolytic Viruses as Cancer Therapeutics Meeting in Banff, Ontario, Mar. 9-13, 2005.

Stanford, et al., "Myxoma Virus Oncolysis of Primary and Metastatic B16F10 Mouse Tumors In Vivo", Molecular Therapy, 16(1): 52-59, Jan. 2008.

Stanford, et al., "Myxoma virus and oncolytic virotherapy: a new biologic weapon in the war against cancer" Expert Opin. Biol. Ther., 7(9):1415-1425, 2007.

Stanford et al., "Rapamycin enhances myxoma virus replication in human tumor cells", Southern Ontario Gene Therapy Meeting in Ontario on Apr. 17-18 2005. (Poster presentation).

Stanford et al., "Rapamycin enhances myxoma virus replication in human tumor cells", Oncolytic Viruses as Cancer Therapeutics meeting in Banff, Alberta, Canada, Mar. 9-12, 2005. (Slides from oral presentation).

U.S. Appl. No. 12/549,939, filed Aug. 28, 2008.

International search report for PCT/US07/70219 dated Jul. 21, 2008.

Written Opinion for PCT/US07/70219 dated Jul. 21, 2008.

Supplementary European search report for EP 07798014 dated Jun. 23, 2010.

Graham, et al., "Myxoma Virus M11L ORF Encodes a Protein for which Cell Surface Localization is Critical in Manifestation of Viral Virulence", Virology, 191:112-124, 1992.

Barrett, et al., "Myxoma virus M063R is a host range gene essential for virus replication in rabbit cells", Virology, 361: 123-132 (2007).

MYXOMA VIRUS MUTANTS FOR CANCER TREATMENT

BACKGROUND OF THE INVENTION

The use of certain genetically modified myxoma viruses for treating cancer is disclosed in WO 04/078206 (Robarts Research Institute).

SUMMARY OF THE INVENTION

This invention relates to Myxoma viruses (MV) that are deficient in the activity of a Myxoma virus protein selected from the group consisting of M11L, M063, M136, M-T4 and M-T7. Such viruses are used in a method for and in the manufacture of a medicament for, inhibiting a cancer cell, which method comprises administering to the cell an effective amount of the Myxoma virus. They are also used in a method for and in the manufacture of a medicament for, treating a human subject having cancer, comprising administering to the patient an effective amount of the Myxoma virus. This invention also provides a pharmaceutical composition comprising such Myxoma viruses and a pharmaceutically acceptable carrier, as well as a kit comprising such Myxoma viruses and instructions for treating a cancer patient.

DETAILED DESCRIPTION OF THE INVENTION

WO 04/078206 (Robarts Research Institute) discloses the use of certain genetically modified myxoma viruses for treating cancer. This invention represents an advance by providing more specific modified myxoma viruses for such uses. The techniques disclosed therein are applicable generally to the myxoma viruses of this invention and the contents of WO 04/078206 are incorporated herein by reference.

As used herein "deficient in the activity of" a given Myxoma virus protein means that the virus has less of the activity in question than wild-type Myxoma virus. "Substantially no activity" of a given viral protein means that the virus has no detectable level of such activity. Examples of Myxoma viruses having substantially no activity of a given viral protein include mutants in which the gene for such protein has been deleted or otherwise knocked-out.

In accordance with this invention, any kind of cancer or cancer cell can be inhibited or treated. In an embodiment of this invention, the cancer cell is a mammalian cancer cell. In a more specific embodiment, the cancer cell is a human cancer cell. Examples of such human cancer cells include gliomas.

It has been demonstrated that wild-type myxoma virus (vMyxgfp) can produce a productive, long-lived infection, and destroy and clear implanted tumor tissue when injected intratumorally into human gliomas implanted in murine brains (Lun et al, 2005 Cancer Research 65:9982-9990). As well, a screen of the NCI-60 reference collection indicated that MV productively infects the majority (15/21) of human tumor cells tested (Sypula et al. 2004 Gene Ther. Mol. Biol. 8:103-114). To expand understanding of MV tropism in cancer cells, a series of human glioma cells (U87, U118, U251, U343, U73) that were previously tested for wild-type MV permissiveness were screened. These findings have been extended in the following Examples by testing the infection and replication of several MV viruses in which specific host range genes, identified as having a role in defining MV tropism in rabbit cells, have been deleted. These viruses are collectively referred to as host range knockouts (vMyx-hrKO). Variation was observed in the ability of various vMyx-hrKOs to replicate and spread in the human glioma cells. vMyxT2 (U251), vMyxT4KO (U87, U118, U251 and U373) and vMyxT5KO (U251, U373) exhibited some restriction in specific human gliomas. In contrast vMyx63KO and vMyx135KO appeared to replicate and kill more effectively in several of the gliomas.

The invention will be better understood by reference to the following examples, which illustrate but do not limit the invention described herein.

EXAMPLES

Example 1

Fifty micrograms of whole cell lysates were probed with antibodies against phosphorylated Akt at positions threonine 308 (P-Akt T308) and serine 473 (P-Akt S473) or total Akt. Based on the levels of activated Akt U87 and U343 would be expected to be infectable and U118, U251 and U373 to be more resistant to MV infection. (FIG. 1).

Example 2

Virus stocks were titrated on the various glioma cells and control BGMK or RK13 cells. Virus titres, derived from the gliomas, were compared to the control levels and a value of viral replication efficiency was estimated. Based on these results none of the gliomas supported viral growth to the levels observed in the control lines. However some viruses (vMyx135KO, vMyx63KO and vMyx136KO) were more efficient than other knockouts. As well, some glioma lines supported more replication (U87, U343 and U373). (FIG. 2)

Example 3

Various human gliomas were infected with a range of vMyx-hrKOs. Twenty hpi the infected supernatants were collected and concentrated 10×. Fifteen microliters of concentrated sups were separated on a 12% SDS-PAGE gel and probed with anti-Serp1 (mAB; late MV gene product). The blots were stripped and probed for early gene expression with anti-M-T7 (pAB; early MV gene product). The results suggest that several vMyx-hrKOs are restricted in their transit from early to late gene expression including vMyxT2KO, vMyxT4KO and vMyxT5KO. And in two glioma lines (U87 and U37), vMyxT4KO does not even undergo early gene expression. (FIG. 3).

Example 4

Figure 1:
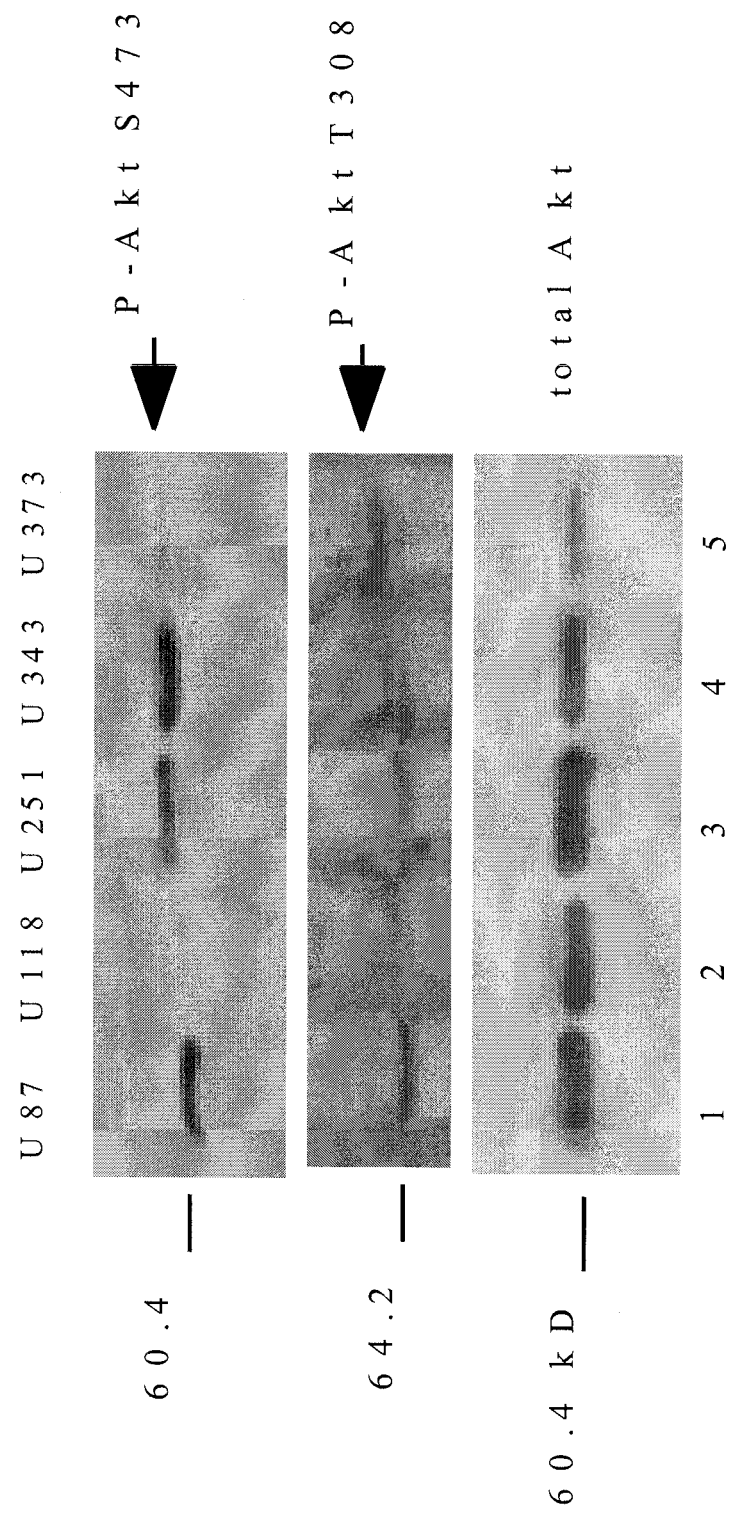
FIG. 1. Endogenous activated Akt levels in human glioma cells
Figure 2:
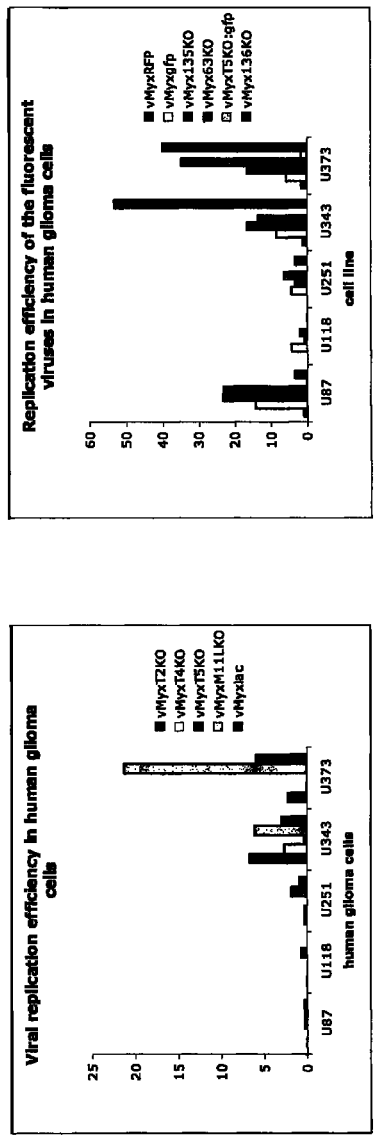
FIG. 2. Viral replication efficiency of the various vMyx-hrKOs and controls in human glioma cell lines.
Figure 3:
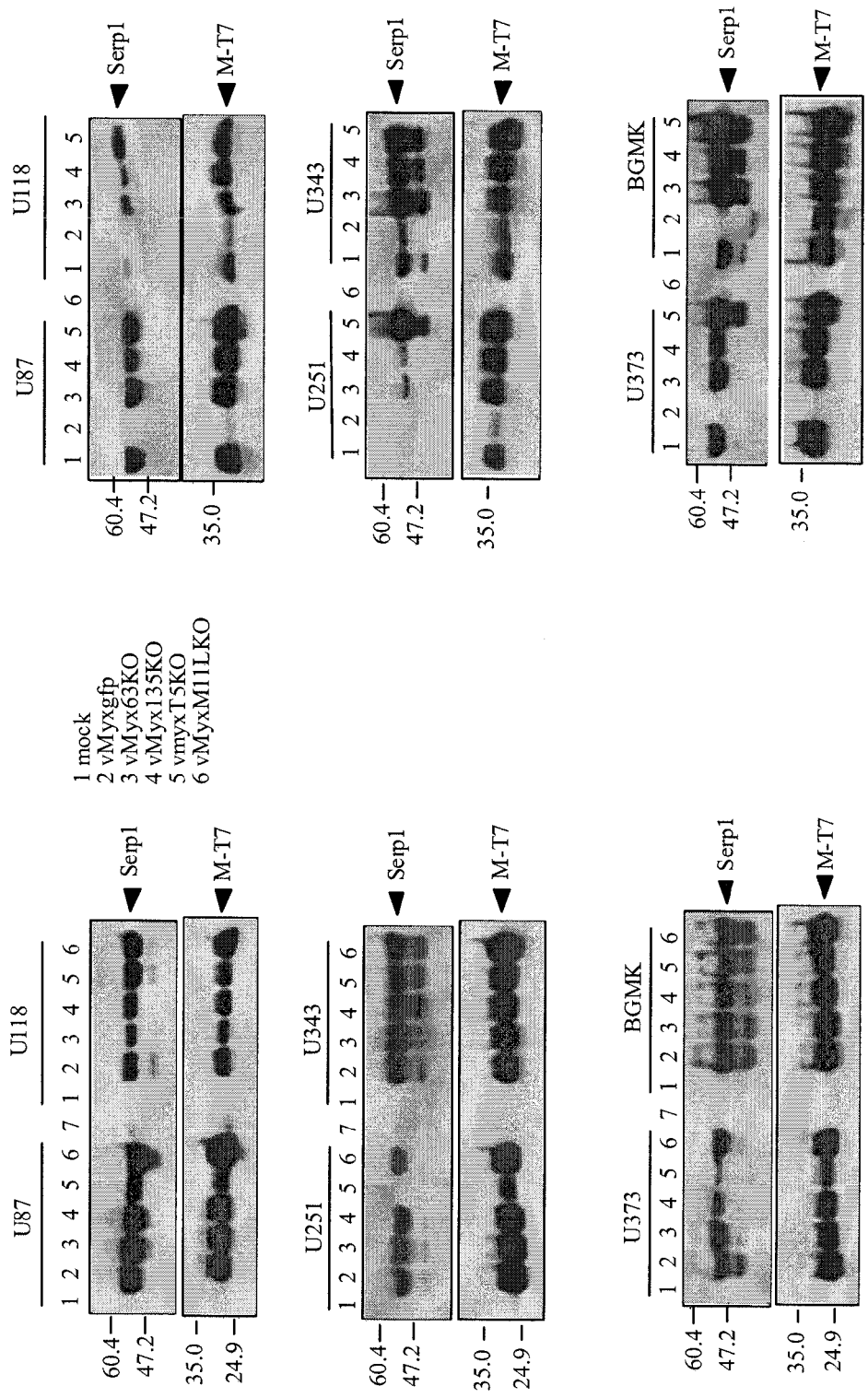
FIG. 3. Secreted early and late viral gene expression indicates that some of the vMyx-hrKO are unable to transit from early to late gene expression.
Figure 4:
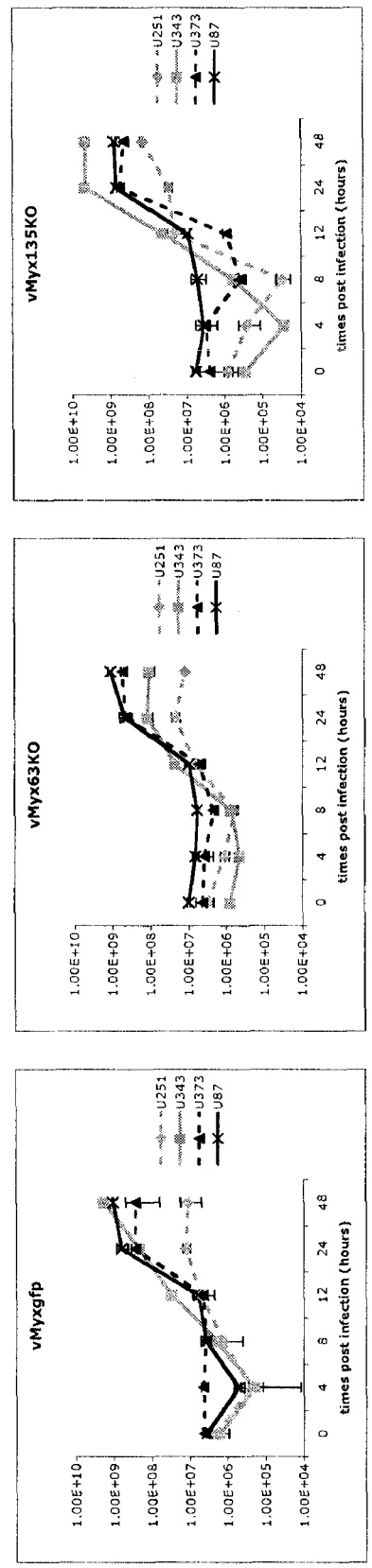
FIG. 4. Selected single step growth curves.

Cells were seeded in 48 well dishes and infected cells were collected at the times indicated. Virus was released from the collected cell pellets and titrated back onto BGMK cells. Although there was replication of the tested viruses, the best amplification appeared to occur in the U87 and U343 cells. (FIG. 4).

Example 5

Figure 5:
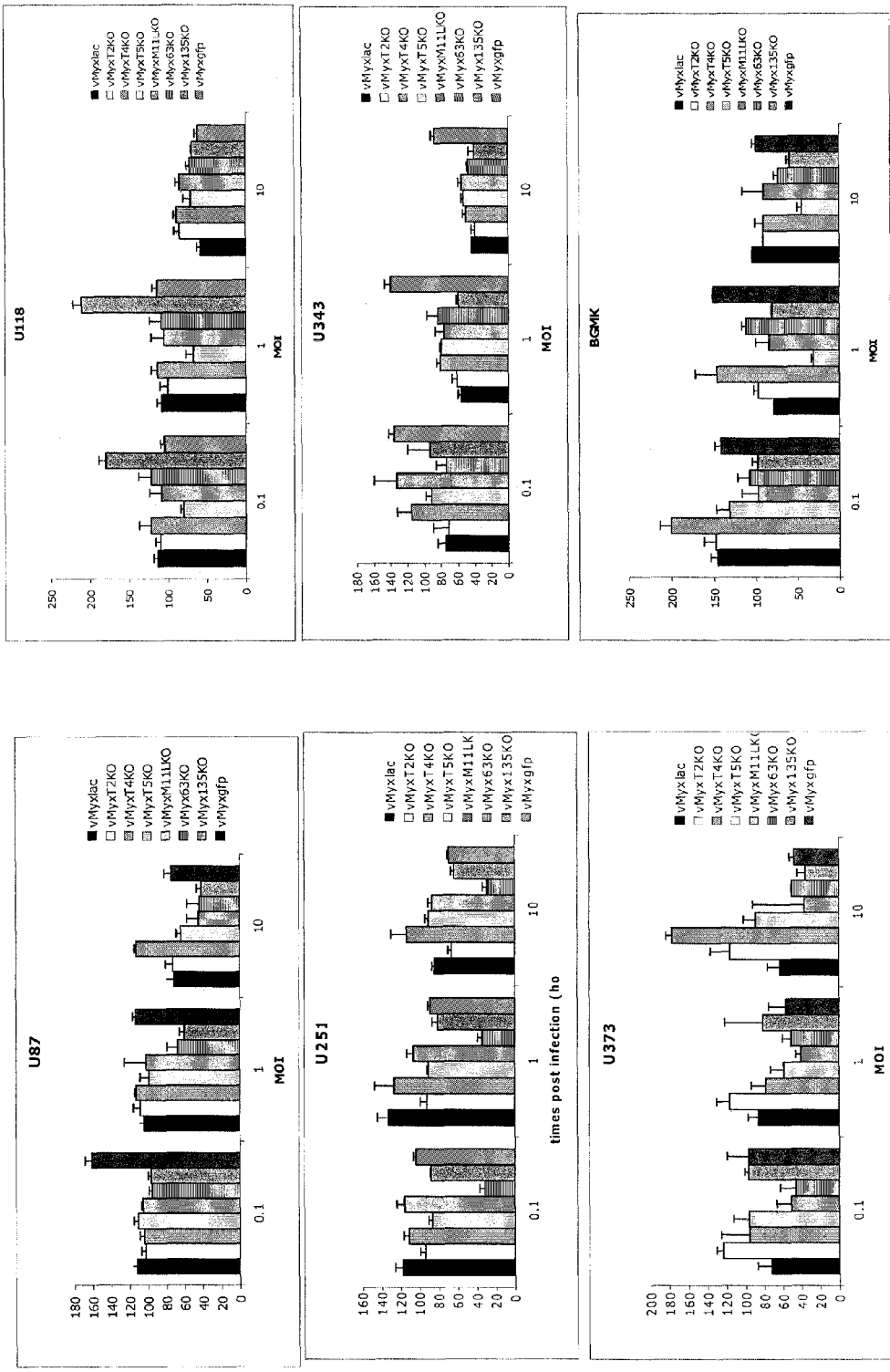
FIG. 5. Cell-based cytotoxicity assay

The ability of the various vMyx-hrKOs and control viruses to have a killing effect in the panel of human gliomas was tested by a cytotoxicity assay. The appropriate cells were seeded in 96 well dishes and 24 h later were infected with the viruses at various MOIs. Seventy-two hours post infection the infected cells were treated with the WTS reagent (Roche) to measure cell viability. Colour changes were measured at 450 nm every 60 minutes for 4 hours. Uninfected control wells were used to determine normal proliferation and a blank well served as a background control. (FIG. 5).

What is claimed is:

1. A pharmaceutical composition comprising a Myxoma virus and a pharmaceutically acceptable carrier, wherein the Myxoma virus has substantially no host range activity of a Myxoma virus protein M063.

2. A kit comprising a Myxoma virus and instructions for treating a patient having cancer, wherein the Myxoma virus has substantially no host range activity of a Myxoma virus protein M063 and the cancer is a glioma.

3. An isolated Myxoma virus that is deficient in the host range activity of a Myxoma virus protein M063.

4. The isolated Myxoma virus of claim 3, wherein the Myxoma virus has substantially no host range activity of the Myxoma virus protein.

5. A method for inhibiting a cancer cell comprising administering to the cell an effective amount of a Myxoma virus that has substantially no host range activity of a Myxoma virus protein M063, wherein the cancer cell is a glioma cell.

* * * * *